United States Patent
Kumar et al.

(10) Patent No.: US 10,661,738 B2
(45) Date of Patent: May 26, 2020

(54) METHOD, SYSTEM, AND DEVICE FOR CONTROLLING INTERNAL SYSTEMS WITHIN A VEHICLE BASED ON USER PREFERENCES

(71) Applicant: WIPRO LIMITED, Bangalore (IN)

(72) Inventors: Vijay Kumar, Bangalore (IN); Thomas Chittakattu Ninan, Angadikadavu (IN); Shagun Rai, Alllahabad (IN)

(73) Assignee: Wipro Limited, Bangalore (IN)

( * ) Notice: Subject to any disclaimer, the term of this patent is extended or adjusted under 35 U.S.C. 154(b) by 130 days.

(21) Appl. No.: 15/901,086

(22) Filed: Feb. 21, 2018

(65) Prior Publication Data
US 2019/0202386 A1    Jul. 4, 2019

(30) Foreign Application Priority Data
Jan. 2, 2018    (IN)    ............................. 201841000186

(51) Int. Cl.
*A61B 5/00*    (2006.01)
*B60N 2/00*    (2006.01)
(Continued)

(52) U.S. Cl.
CPC .......... *B60R 16/037* (2013.01); *A61B 5/6892* (2013.01); *B60N 2/002* (2013.01); *B60N 3/04* (2013.01); *B60N 3/048* (2013.01); *G01S 17/88* (2013.01); *A61B 5/1036* (2013.01); *A61B 5/1074* (2013.01); *G01S 17/04* (2020.01); *G01V 3/00* (2013.01)

(58) Field of Classification Search
CPC .......... A61B 5/00; A61B 5/6892; B60N 2/00; B60N 2/002; B60N 3/00; B60N 3/04; B60N 3/048; H04W 4/00; H04W 4/025; G01S 17/00; G01S 17/88
See application file for complete search history.

(56) References Cited

U.S. PATENT DOCUMENTS

| | | | |
|---|---|---|---|
| 6,450,886 B1 | 9/2002 | Oishi et al. | |
| 6,916,997 B2 * | 7/2005 | Thakur | .............. G01G 19/4142 |
| | | | 177/136 |

(Continued)

FOREIGN PATENT DOCUMENTS

WO    2009081113 A2    7/2009

OTHER PUBLICATIONS

Extended European Search Report issued in the European Patent Office in counterpart European Application No. 18164419.6, dated Sep. 28, 2018, 8 pages.

*Primary Examiner* — Yonel Beaulieu
(74) *Attorney, Agent, or Firm* — Finnegan, Henderson, Farabow, Garrett & Dunner, LLP

(57) ABSTRACT

A method, system, and device for controlling internal systems within a vehicle based on user preferences is disclosed. The method includes detecting, by a floor mat, presence of a user seated on a seat within the vehicle. The method further includes capturing, by the floor mat, at least one user characteristic associated with the user in response to detecting presence of the user. The method includes controlling, by the floor mat, at least one internal system within the vehicle based on the at least one user characteristic, wherein the floor mat communicates with a central controller in the vehicle to control the at least one internal system.

17 Claims, 6 Drawing Sheets

(51) Int. Cl.
  *B60N 3/00*       (2006.01)
  *B60N 3/04*       (2006.01)
  *H04W 4/00*       (2018.01)
  *G01S 17/00*      (2020.01)
  *G01S 17/88*      (2006.01)
  *B60R 16/037*     (2006.01)
  *G01S 17/04*      (2020.01)
  *A61B 5/103*      (2006.01)
  *A61B 5/107*      (2006.01)
  *G01V 3/00*       (2006.01)

(56) References Cited

U.S. PATENT DOCUMENTS

| | | | | |
|---|---|---|---|---|
| 7,436,325 | B2* | 10/2008 | Bailey | B60N 3/04 341/176 |
| 8,106,796 | B2* | 1/2012 | Bailey | B60N 3/04 341/20 |
| 2003/0039298 | A1 | 2/2003 | Eriksson et al. | |
| 2003/0106723 | A1* | 6/2003 | Thakur | G01G 19/4142 177/144 |
| 2006/0290518 | A1* | 12/2006 | Bingle | E05B 83/26 340/573.1 |
| 2008/0157940 | A1* | 7/2008 | Breed | B60C 11/24 340/425.5 |
| 2012/0018240 | A1* | 1/2012 | Grubaugh | B60T 7/14 180/273 |
| 2014/0052343 | A1 | 2/2014 | Chen | |
| 2015/0307040 | A1* | 10/2015 | Heyden | B60K 35/00 340/449 |
| 2015/0319608 | A1* | 11/2015 | Varughese | H04W 4/046 455/456.4 |
| 2016/0027079 | A1* | 1/2016 | Schoeffler | H04N 5/23293 705/325 |
| 2016/0128623 | A1 | 5/2016 | Bhat | |
| 2016/0173440 | A1* | 6/2016 | Stahura | G06F 16/9537 709/245 |
| 2017/0305301 | A1* | 10/2017 | McMillen | B60N 2/002 |
| 2017/0356815 | A1 | 12/2017 | Madden et al. | |
| 2018/0068544 | A1* | 3/2018 | Caperell | G08B 21/22 |
| 2018/0348759 | A1* | 12/2018 | Freeman | G05D 1/0061 |

* cited by examiner

METHOD, SYSTEM, AND DEVICE FOR CONTROLLING INTERNAL SYSTEMS WITHIN A VEHICLE BASED ON USER PREFERENCES

TECHNICAL FIELD

This disclosure relates generally to vehicles and more particularly to method, system, and device for controlling internal systems within a vehicle based on user preferences.

BACKGROUND

Floor mats of the "throw-in" or accessory type are popularly used to protect carpeted floor of vehicles. Such mats are generally manufactured with a planar configuration and are customarily made of a material sufficiently flexible to conform, when placed in use, to the multiplicity of shapes and contours characteristic of vehicle floors. Moreover, almost all floor mats found in motor vehicles today merely protect the floor of the vehicle from getting damaged due to dirt from the user's feet. Such limited use of floor mats ignores their potential to act as information processing centers and controllers for other devices.

SUMMARY

In one embodiment, a method for controlling internal systems within a vehicle is disclosed. The method includes detecting, by a floor mat, presence of a user seated on a seat within the vehicle. The method further includes capturing, by the floor mat, at least one user characteristic associated with the user in response to detecting presence of the user. The method includes controlling, by the floor mat, at least one internal system within the vehicle based on the at least one user characteristic, wherein the floor mat communicates with a central controller in the vehicle to control the at least one internal system.

In another embodiment, a floor mat for controlling internal systems within a vehicle is disclosed. The floor mat includes at least one senor configured to detect presence of a user seated on a seat within the vehicle and to capture at least one user characteristic associated with the user in response to detecting presence of the user. The floor mat further includes a communication interface communicatively coupled to the at least one sensor. The communication interface is configured to transmit at least one user characteristic to a central controller, wherein the central controller control at least one internal system within the vehicle based on the at least one user characteristic.

In yet another embodiment, a system for controlling internal systems within a vehicle is disclosed. The system includes a floor mat comprising at least one senor configured to detect presence of a user seated on a seat within the vehicle and to capture at least one user characteristic associated with the user in response to detecting presence of the user. The system further includes a central controller communicatively coupled the floor mat. The central controller is configured to control at least one internal system within the vehicle based on the at least one user characteristic.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. Wherever convenient, the same reference numbers are used throughout the drawings to refer to the same or like parts. While examples and features of disclosed principles are described herein, modifications, adaptations, and other implementations are possible without departing from the spirit and scope of the disclosed embodiments. It is intended that the following detailed description be considered as exemplary only, with the true scope and spirit being indicated by the following claims.

Figure 1:
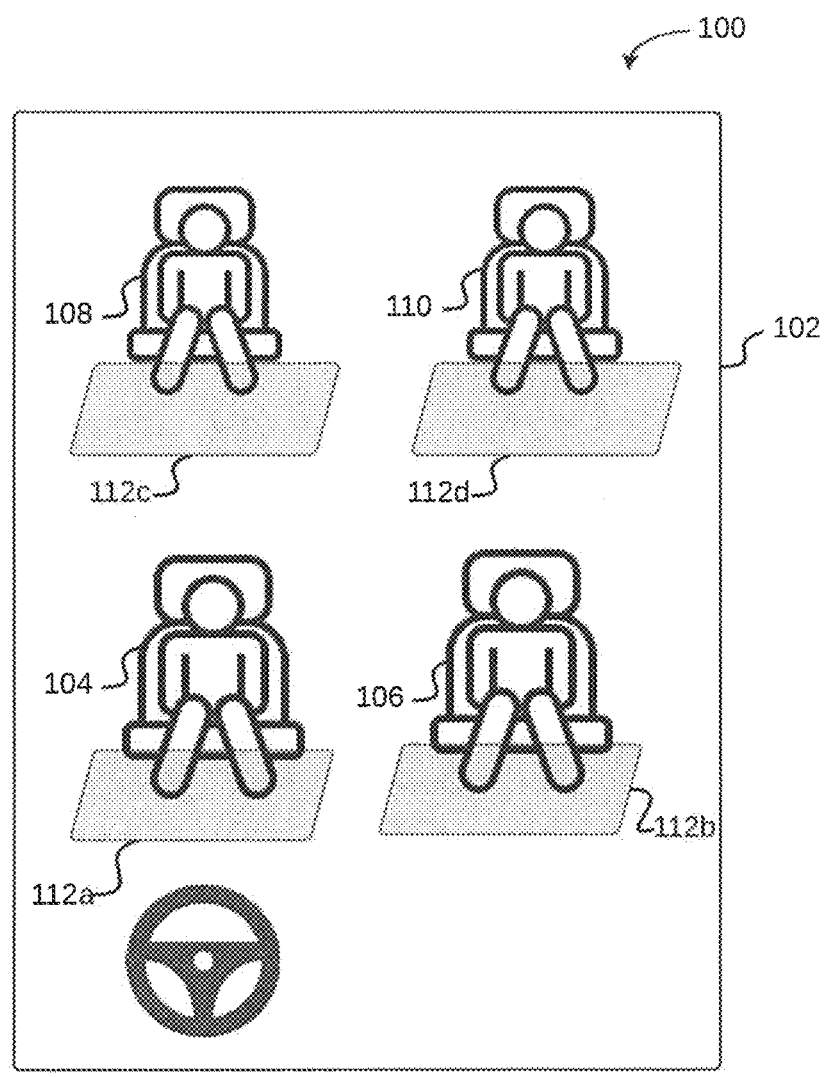
FIG. 1 is a block diagram illustrating an environment in which various embodiment may be employed.

Additional illustrative embodiments are listed below. In one embodiment, an environment 100 (that is exemplary) in which various embodiments may be employed is illustrated in FIG. 1. Environment 100 includes a vehicle 102 in which a driver 104 is sitting along with a passenger 106 sitting beside driver 104 and passengers 108 and 110 sitting on the back seat of vehicle 102. Vehicle 102 may be an autonomous vehicle. Examples of vehicles may include, but are not limited to a car, bus, a truck, an airplane, or a train.

Vehicle 102 include a plurality of internal systems (not shown in FIG. 1). Examples of the internal systems may include, but are not limited to heating and air-conditioning system, deodorizer, audio system, ambient lights, fan, seat vibration system, backrest heating system, seat height, length or inclination. These internal systems are either manually controlled by driver 104 or passengers 106, 108, and 110. The internal systems may be automatically controlled, however, this automatic control is not based on personal preference of passengers 106, 108, and 110, or driver 104.

In order to provide a personalized experience, floor mats 112*a*, 112*b*, 112*c*, and 112*d* may be provided inside vehicle 102, such that, floor mat 112*a* is placed below the seat of driver 104 and floor mats 112*b*, 112*c*, and 112*d* are respectively placed below seats of passengers 106, 108, and 110. Floor mats 112*a*, 112*b*, 112*c*, and 112*d* measure one or more user characteristics associated with respective passengers or driver, based on which, one or more of the internal systems may be controlled. This is further explained in detail in conjunction with FIG. 2. It will be apparent to a person skilled in the art that though floor mats 112*a*, 112*b*, 112*c*, and 112*d* have been depicted in separate portions, they may be arranged such that they form a single floor mat placed on floor of vehicle 102.

Figure 2:
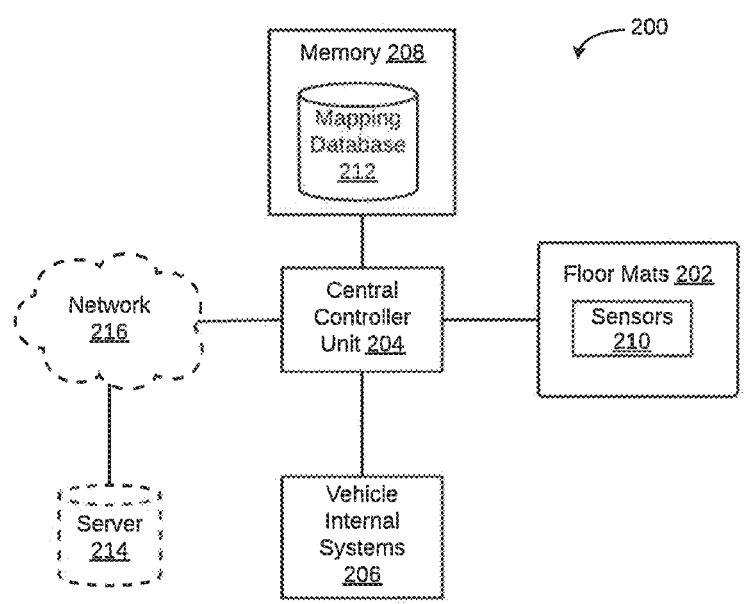
FIG. 2 is a block diagram illustrating a system for controlling internal systems within a vehicle based on user preferences, in accordance with an embodiment.

Referring now to FIG. 2, is a block diagram illustrating a system 200 for controlling internal systems within a vehicle based on user preferences, in accordance with an embodiment. System 200 may include floor mats 202 that are in communication with a central controller unit 204. Floor mats 202 are analogous to floor mats 112a, 112b, 112c, and 112d. Central controller unit 204 may further communicate with vehicle internal systems 206 and a memory 208. Memory 208 may be volatile memory or non-volatile memory. Examples of non-volatile memory, may include, but are not limited to a flash memory, a Read Only Memory (ROM), a Programmable ROM (PROM), Erasable PROM (EPROM), and Electrically EPROM (EEPROM) memory. Examples of volatile memory may include, but are not limited Dynamic Random Access Memory (DRAM), and Static Random-Access memory (SRAM).

Floor mats 202 includes one or more sensors 210 that may detect presence of users or passengers inside the vehicle. Once presence of one or more users is detected, one or more sensors 210 may capture one or more user characteristics, which include, but are not limited to one or more of size of a user's foot, weight of a user's foot, shape of a user's foot, or pressure points activated by a user's foot on the floor mat. A given floor mat may only capture user characteristics associated with a user sitting on a seat below which the floor mat is placed.

One or more sensors 210 may include a resistive mesh that detects user presence and captures one or more user characteristics based on resistance change in the resistive mesh. The resistance change is caused when a user places his foot or feet on one of floor mats 202. Additionally, one or more sensors 210 may include a Light Detection and Ranging (LIDARs), which may detect presence of a user whose foot is not in contact with the resistive mesh. By way of an example, a child sitting on a seat within the vehicle would not be able to touch one of floor mats 202. In this case, the LIDAR may detect presence of the child and capture one or more user characteristics associated with the child.

Once floor mats 202 detect presence of one or more users inside the vehicle, floor mats 202 communicate the one or more user characteristics captured for one or more users to central controller unit 204 through a communication interface (not shown in FIG. 2). Thereafter, central controller unit 204 communicates with memory 208, which includes details associated with registered users. A user while registering with system 200 may provide various details to system 200. These details may include one or more user characteristics and preferences associated with the user. The preferences, for example, may include one or more of cabin temperature, deodorizer settings, sound level of audio system, light intensity, fan speed, seat vibration, backrest heating, seat height, length or inclination. Memory 208 may store mapping between user characteristics and user preferences for a plurality of registered users in a mapping database 212.

Thus, central controller unit 204 may match the one or more user characteristics captured by one or more sensors 210 in floor mats 202, with user characteristics stored in mapping database 212. This is further explained in detail in conjunction with FIGS. 3 and 5. In an alternate embodiment, once central controller unit 204 receives one or more user characteristics captured by one or more sensors 210, central controller unit 204 may communicate with a server 214 via a network 216. This embodiment would be more relevant in the case of a public transport vehicle, for example, a bus, a train, or an airplane. As a given user may not always travel the same public transport vehicle, mapping database 212 may be stored in server 214 that can be accessed by multiple central controller units across different vehicles. Network 216 may be a wired or a wireless network and the examples may include, but are not limited to the Internet, Wireless Local Area Network (WLAN), Wi-Fi, Long Term Evolution (LTE), Worldwide Interoperability for Microwave Access (WiMAX), and General Packet Radio Service (GPRS). In this embodiment, server 214 may include mapping database 212 and mappings in mapping database 212 may not be limited to a single vehicle.

Figure 3:
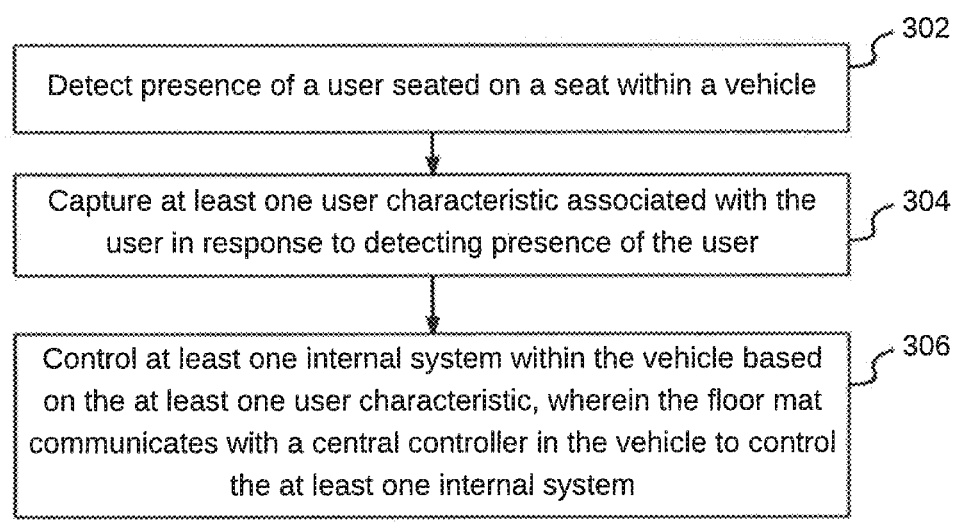
FIG. 3 illustrates a flowchart of a method for controlling internal systems within a vehicle, in accordance with an embodiment.

Referring now to FIG. 3, a flowchart of a method for controlling internal systems within a vehicle is illustrated, in accordance with an embodiment. The internal systems, for example, may include, but are not limited to heating and air-conditioning system, deodorizer, audio system, ambient lights, fan, seat vibration system, backrest heating system, seat height, length or inclination.

At step 302, one of floor mats 202 may detect presence of a user seated on a seat within the vehicle. The presence of the user may be detected by one or more sensors 210, which may be a resistive mesh, when a foot of the user is in physical contact with one of floor mats 202. In other words, the foot of the user is resting on one of floor mats 202. Alternatively, presence of the user may be detected by a LIDAR, when a foot of the user is not in physical contact with one of floor mats 202. By way of an example, in case a child is sitting on a seat in the vehicle, a LIDAR and not a resistive mesh will detect presence of the child inside the vehicle.

Once presence of the user is detected, one of floor mats 202 captures one or more user characteristics associated with the user at step 304. The one or more user characteristics may include one or more of, but are not limited to size of a user's foot, weight of a user's foot, shape of a user's foot, or pressure points activated by a user's foot on the floor mat. In other words, user characteristics are associated with feet of a user sitting inside the vehicle. The one or more user characteristics may be captured by a resistive mesh, when after a user places his/her foot, resistance of the resistive mesh at the contact area changes. This area may be in correlation with foot characteristics (for example, foot size and shape) of the user. In an embodiment, other characteristics of the user, for example, weight, voice, or posture, etc, may also be captured, in order to do accurately identify a user.

Based on the one or more user characteristics, one of floor mats 202 controls one or more internal systems within the vehicle at step 306. To this end, one of floor mats 202 communicates with central controller unit 204 in the vehicle. This has already been explained in conjunction with FIG. 2. The decisions taken by central controller unit 204 to control activation and deactivation of one or more internal systems is further explained in detail in conjunction with FIG. 5.

Figure 4:
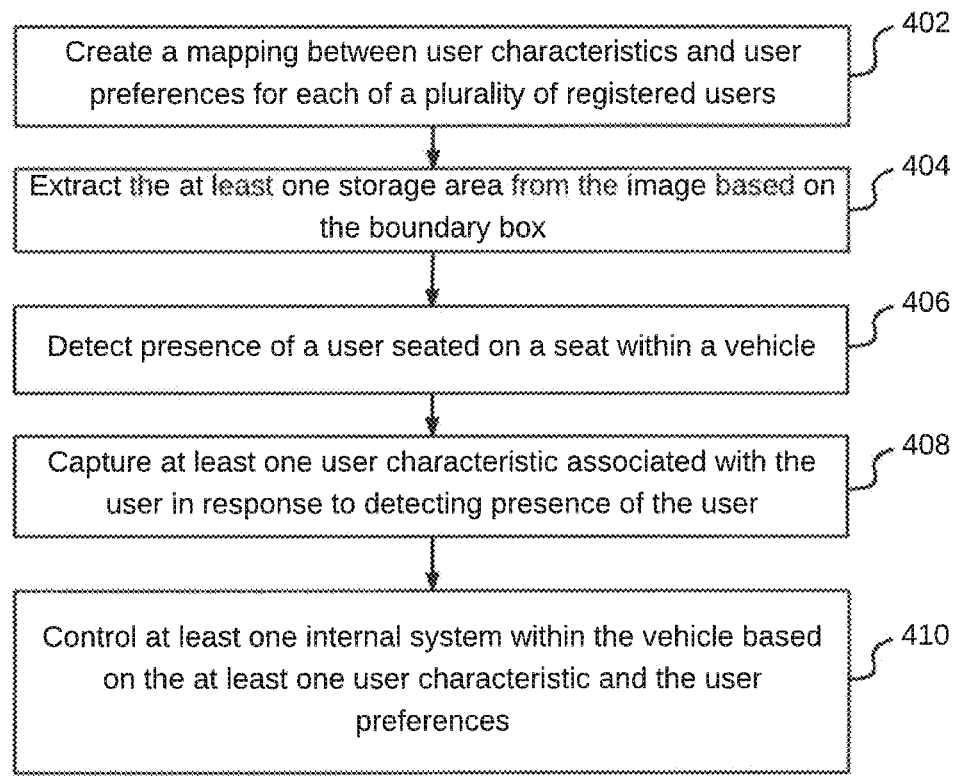
FIG. 4 illustrates a flowchart of a method for controlling internal systems within a vehicle based on user preferences, in accordance with an embodiment.

Referring now to FIG. 4, a flowchart of a method for controlling internal systems within a vehicle based on user preferences is illustrated, in accordance with an embodiment. For a given vehicle, a plurality of users may be registered with system 200 of the vehicle. In order to register a user, one or more user characteristics may first be capture for a given user. Thereafter, the user may be required to provide detail regarding one or more preferences. The one or more preferences may include, but are not limited to cabin temperature, deodorizer settings, sound level of audio system, light intensity, fan speed, seat vibration, backrest heating, seat height, length or inclination. Based on these detail capture for a plurality of registered users, a mapping between user characteristics and user preferences for each of the plurality of registered users may be created at step 402.

The mapping may then be stored inside a storage device (for example, memory 208) within the vehicle for the plurality of registered users at step 404. The storage device may be communicatively coupled with central controller unit 204. Thereafter, when a user enters the vehicle and sits on one of the seats inside the vehicle, presence of the user within the vehicle may be detected at step 406. This has been explained in conjunction with FIG. 3.

Once presence of the user is detected, one or more user characteristics associated with the user may be captured at step 408. The one or more user characteristics may include one or more of, but are not limited to size of a user's foot, weight of a user's foot, shape of a user's foot, or pressure points activated by a user's foot on a floor mat. Based on the one or more user characteristics and user preferences that are mapped to the one or more user characteristics, one or more internal systems within the vehicle may be controlled at step 410. This is further explained in detail in conjunction with FIG. 5.

Figure 5:
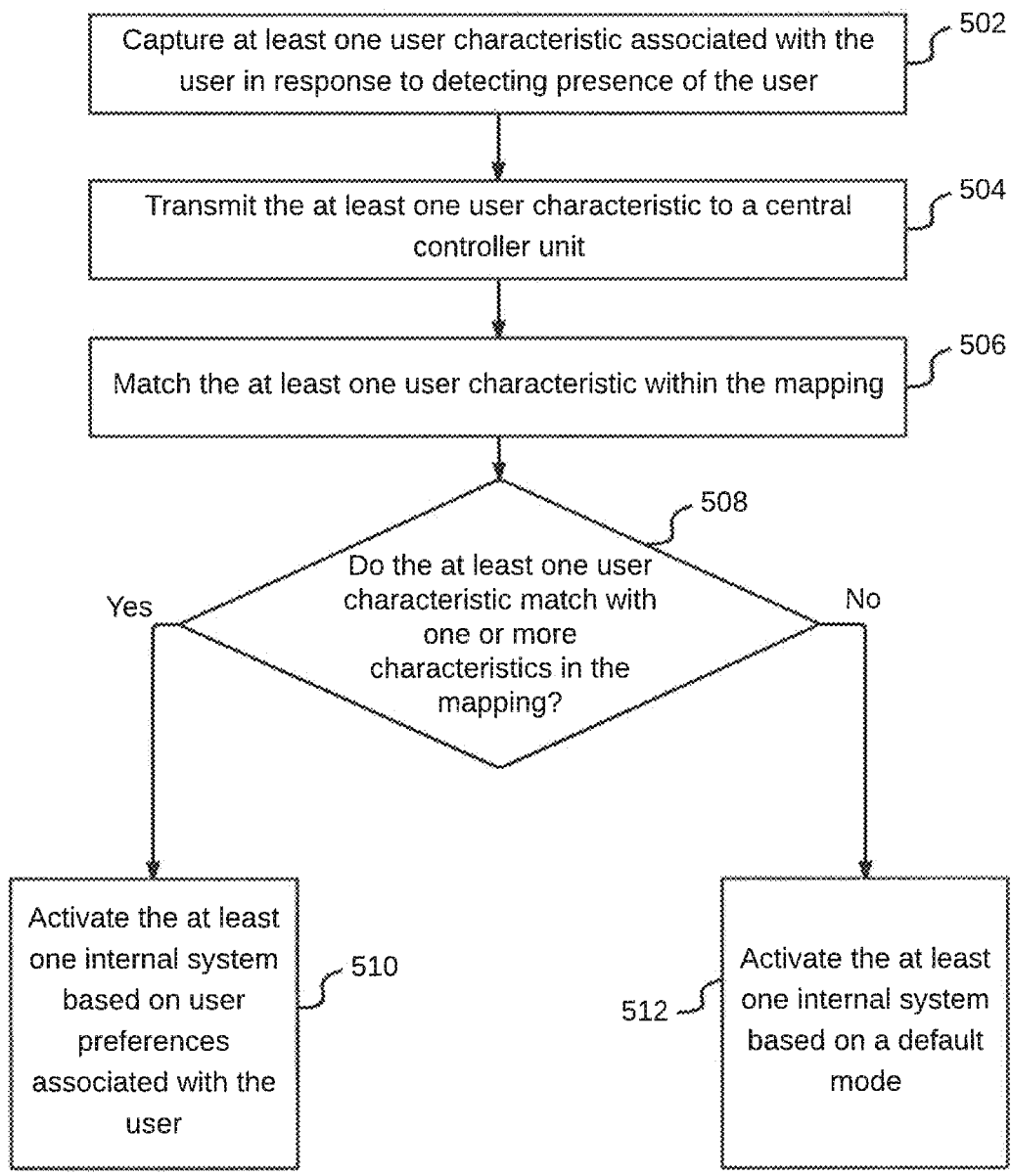
FIG. 5 illustrates a flowchart of a method for determining a mode of activating one or more internal systems within a vehicle based on user characteristics and a mapping database, in accordance with an embodiment.

Referring now to FIG. 5, a flowchart of a method for determining a mode of activating one or more internal systems within a vehicle based on user characteristics and a mapping database is illustrated, in accordance with an embodiment. At step 502, in response to detecting presence of a user inside the vehicle, one or more user characteristics associated with the user may be captured. The one or more user characteristics may be captured by one of floor mats 202. At step 504, the captured one or more user characteristics may be transmitted to central controller unit 204.

Thereafter, at step 506, central controller unit 204 may match the one or more user characteristics within the mapping stored in mapping database 212. The matching is done in order to determine whether one or more internal systems in the vehicle need to be turned on or off. At step 508, central controller unit 204 may perform a check to determine whether the one or more characteristics captured for a user match with one or more characteristics stored in the mapping in mapping database 212. In other words, a check is performed to determine whether the user sitting in the vehicle is a registered user or not.

When central controller unit 204 find a match in mapping database 212, central controller unit 204 activates the one or more internal systems based on user preferences associated with the user at step 510. In other words, the user inside the vehicle is a registered user and thus user preferences for that user are stored in mapping database 212. By way of an example, while registering with system 200, foot size and shape of a user may be captured by one or more sensors 210. Thereafter, the user may provide the following user preferences to system 200: low volume for vehicle audio system, cabin temperature at a constant 26 degrees, and ambient light to be switched off while the vehicle is moving. In response, the user is registered with system 200 and a mapping of the one or more characteristics with the user preferences is created in mapping database 212. Thus, when this registered user enters the vehicle, one or more sensors 210 capture the foot size and shape of the registered user and central controller unit 204 matches the foot size and shape with user characteristics stored in mapping database 212. When central controller unit 204 finds the same foot size and shape, it retrieves the mapped user preferences and implements the same. In other words, central controller unit 204 activates the following: low volume for vehicle audio system, cabin temperature at a constant 26 degrees, and ambient light to be switched off while the vehicle is moving. Thus, internal systems of the vehicle are customized or personalized based on the users identified inside the vehicle.

Referring back to step 508, when central controller unit 204 does not find a match in mapping database 212, central controller unit 204 activates the one or more internal systems based on a default mode at step 512. In other words, the user is an unregistered user. The default mode may include default values for all internal systems. These default values may be prefixed by a system administrator or owner of the vehicle. Additionally, when central controller unit 204 does not find a match in mapping database 212, central controller unit 204 may prompt the unregistered user to provide his/her user preferences and may store a mapping between the captured one or more user characteristics and the provided user preferences in mapping database 212.

Figure 6:
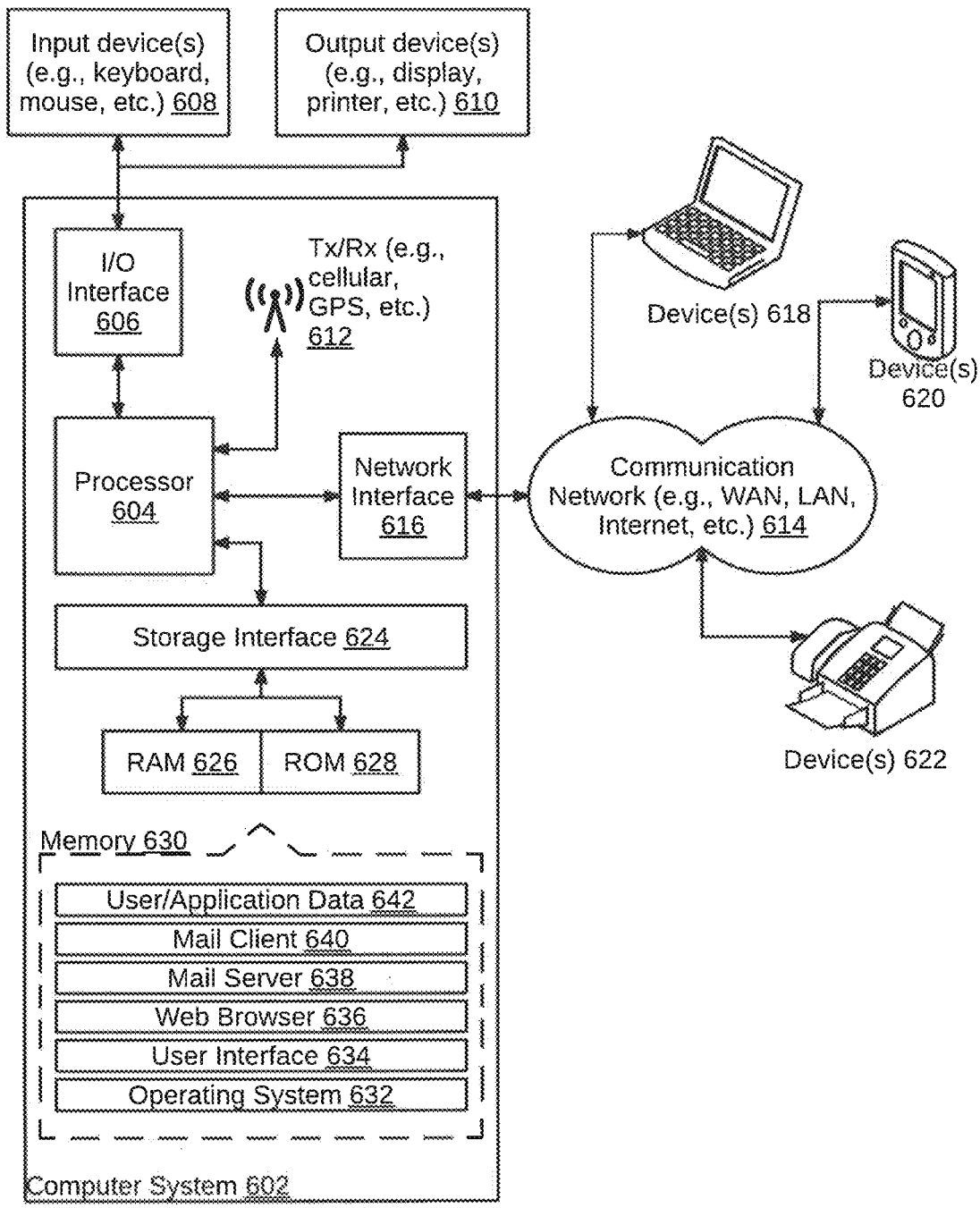
FIG. 6 illustrates a block diagram of an exemplary computer system for implementing various embodiments.

FIG. 6 is a block diagram of an exemplary computer system for implementing various embodiments. Computer system 602 may include a central processing unit ("CPU" or "processor") 604. Processor 604 may include at least one data processor for executing program components for executing user- or system-generated requests. A user may include a person, a person using a device such as such as those included in this disclosure, or such a device itself. Processor 604 may include specialized processing units such as integrated system (bus) controllers, memory management control units, floating point units, graphics processing units, digital signal processing units, etc. Processor 604 may include a microprocessor, such as AMD® ATHLON® microprocessor, DURON® microprocessor OR OPTERON® microprocessor, ARM's application, embedded or secure processors, IBM® POWERPC®, INTEL'S CORE® processor, ITANIUM® processor, XEON® processor, CELERON® processor or other line of processors, etc. Processor 604 may be implemented using mainframe, distributed processor, multi-core, parallel, grid, or other architectures. Some embodiments may utilize embedded technologies like application-specific integrated circuits (ASICs), digital signal processors (DSPs), Field Programmable Gate Arrays (FPGAs), etc.

Processor 604 may be disposed in communication with one or more input/output (I/O) devices via an I/O interface 606. I/O interface 606 may employ communication protocols/methods such as, without limitation, audio, analog, digital, monoaural, RCA, stereo, IEEE-1394, serial bus, universal serial bus (USB), infrared, PS/2, BNC, coaxial, component, composite, digital visual interface (DVI), high-definition multimedia interface (HDMI), RF antennas, S-Video, VGA, IEEE 802.n/b/g/n/x, Bluetooth, cellular (e.g., code-division multiple access (CDMA), high-speed packet access (HSPA+), global system for mobile communications (GSM), long-term evolution (LTE), WiMax, or the like), etc.

Using I/O interface 606, computer system 602 may communicate with one or more I/O devices. For example, an input device 608 may be an antenna, keyboard, mouse, joystick, (infrared) remote control, camera, card reader, fax machine, dongle, biometric reader, microphone, touch screen, touchpad, trackball, sensor (e.g., accelerometer, light sensor, GPS, gyroscope, proximity sensor, or the like), stylus, scanner, storage device, transceiver, video device/source, visors, etc. An output device 610 may be a printer, fax machine, video display (e.g., cathode ray tube (CRT), liquid crystal display (LCD), light-emitting diode (LED), plasma, or the like), audio speaker, etc. In some embodiments, a transceiver 612 may be disposed in connection with processor 604. Transceiver 612 may facilitate various types of wireless transmission or reception. For example, transceiver 612 may include an antenna operatively connected to a transceiver chip (e.g., TEXAS® INSTRUMENTS WIL- INK WL1283® transceiver, BROADCOM® BCM4550IUB8200 transceiver, INFINEON TECHNOLOGIES® X-GOLD 618-PMB9800® transceiver, or the like), providing IEEE 802.11a/b/g/n, Bluetooth, FM, global positioning system (GPS), 2G/3G HSDPA/HSUPA communications, etc.

In some embodiments, processor 604 may be disposed in communication with a communication network 614 via a network interface 616. Network interface 616 may communicate with communication network 614. Network interface 616 may employ connection protocols including, without limitation, direct connect, Ethernet (e.g., twisted pair 50/500/5000 Base T), transmission control protocol/internet protocol (TCP/IP), token ring, IEEE 802.11a/b/g/n/x, etc. Communication network 614 may include, without limitation, a direct interconnection, local area network (LAN), wide area network (WAN), wireless network (e.g., using Wireless Application Protocol), the Internet, etc. Using network interface 616 and communication network 614, computer system 602 may communicate with devices 618, 620, and 622. These devices may include, without limitation, personal computer(s), server(s), fax machines, printers, scanners, various mobile devices such as cellular telephones, smartphones (e.g., APPLE® IPHONE® smartphone, BLACKBERRY® smartphone, ANDROID® based phones, etc.), tablet computers, eBook readers (AMAZON® KINDLE® ereader, NOOK® tablet computer, etc.), laptop computers, notebooks, gaming consoles (MICROSOFT® XBOX® gaming console, NINTENDO® DS® gaming console, SONY® PLAYSTATION® gaming console, etc.), or the like. In some embodiments, computer system 602 may itself embody one or more of these devices.

In some embodiments, processor 604 may be disposed in communication with one or more memory devices (e.g., RAM 626, ROM 628, etc.) via a storage interface 624. Storage interface 624 may connect to memory 630 including, without limitation, memory drives, removable disc drives, etc., employing connection protocols such as serial advanced technology attachment (SATA), integrated drive electronics (IDE), IEEE-1394, universal serial bus (USB), fiber channel, small computer systems interface (SCSI), etc. The memory drives may further include a drum, magnetic disc drive, magneto-optical drive, optical drive, redundant array of independent discs (RAID), solid-state memory devices, solid-state drives, etc.

Memory 630 may store a collection of program or database components, including, without limitation, an operating system 632, user interface application 634, web browser 636, mail server 638, mail client 640, user/application data 642 (e.g., any data variables or data records discussed in this disclosure), etc. Operating system 632 may facilitate resource management and operation of computer system 602. Examples of operating systems 632 include, without limitation, APPLE® MACINTOSH® OS X platform, UNIX platform, Unix-like system distributions (e.g., Berkeley Software Distribution (BSD) FreeBSD, NetBSD, OpenBSD, etc.), LINUX distributions (e.g., RED HAT®, UBUNTU®, KUBUNTU®, etc.), IBM® OS/2 platform, MICROSOFT® WINDOWS® platform (XP, Vista/7/8, etc.), APPLE® IOS® platform, GOOGLE® ANDROID® platform, BLACKBERRY® OS platform, or the like. User interface 634 may facilitate display, execution, interaction, manipulation, or operation of program components through textual or graphical facilities. For example, user interfaces may provide computer interaction interface elements on a display system operatively connected to computer system 602, such as cursors, icons, check boxes, menus, scrollers, windows, widgets, etc. Graphical user interfaces (GUIs) may be employed, including, without limitation, APPLE® Macintosh® operating systems' AQUA® platform, IBM® OS/2® platform, MICROSOFT® WINDOWS® platform (e.g., AERO® platform, METRO® platform, etc.), UNIX X-WINDOWS, web interface libraries (e.g., ACTIVEX® platform, JAVA® programming language, JAVASCRIPT® programming language, AJAX® programming language, HTML, ADOBE® FLASH® platform, etc.), or the like.

In some embodiments, computer system 602 may implement a web browser 636 stored program component. Web browser 636 may be a hypertext viewing application, such as MICROSOFT® INTERNET EXPLORER® web browser, GOOGLE® CHROME® web browser, MOZILLA® FIREFOX® web browser, APPLE® SAFARI® browser, etc. Secure web browsing may be provided using HTTPS (secure hypertext transport protocol), secure sockets layer (SSL), Transport Layer Security (TLS), etc. Web browsers may utilize facilities such as AJAX, DHTML, ADOBE® FLASH® platform, JAVASCRIPT® programming language, JAVA® programming language, application programming interfaces (APis), etc. In some embodiments, computer system 602 may implement a mail server 638 stored program component. Mail server 638 may be an Internet mail server such as MICROSOFT® EXCHANGE® mail server, or the like. Mail server 638 may utilize facilities such as ASP, ActiveX, ANSI C++/C#, MICROSOFT .NET® programming language, CGI scripts, JAVA® programming language, JAVASCRIPT® programming language, PERL® programming language, PHP® programming language, PYTHON® programming language, WebObjects, etc. Mail server 638 may utilize communication protocols such as internet message access protocol (IMAP), messaging application programming interface (MAPI), Microsoft Exchange, post office protocol (POP), simple mail transfer protocol (SMTP), or the like. In some embodiments, computer system 602 may implement a mail client 640 stored program component. Mail client 640 may be a mail viewing application, such as APPLE MAIL® mail client, MICROSOFT ENTOURAGE® mail client, MICROSOFT OUTLOOK® mail client, MOZILLA THUNDERBIRD® mail client, etc.

In some embodiments, computer system 602 may store user/application data 642, such as the data, variables, records, etc. as described in this disclosure. Such databases may be implemented as fault-tolerant, relational, scalable, secure databases such as ORACLE® database OR SYBASE® database. Alternatively, such databases may be implemented using standardized data structures, such as an array, hash, linked list, struct, structured text file (e.g., XML), table, or as object-oriented databases (e.g., using OBJECTSTORE® object database, POET® object database, ZOPE® object database, etc.). Such databases may be consolidated or distributed, sometimes among the various computer systems discussed above in this disclosure. It is to be understood that the structure and operation of the any computer or database component may be combined, consolidated, or distributed in any working combination.

It will be appreciated that, for clarity purposes, the above description has described embodiments of the invention with reference to different functional units and processors. However, it will be apparent that any suitable distribution of functionality between different functional units, processors or domains may be used without detracting from the invention. For example, functionality illustrated to be performed by separate processors or controllers may be performed by the same processor or controller. Hence, references to specific functional units are only to be seen as references to suitable means for providing the described functionality, rather than indicative of a strict logical or physical structure or organization.

Various embodiments of the invention provide method, system, and device for controlling internal systems within a vehicle based on user preferences. The system and device automatically control internal systems within a vehicle according to the user presence and preferences, without requiring any manual interventions. In this system, floor mats of the vehicle are equipped with a resistive mesh and/or LIDAR that automatically capture user characteristics associated with a user, when the user sits inside the vehicle. Accordingly, the central controller unit 204 identifies the user and controls various internal systems based on personal preferences of the user.

The specification has described provide method, system, and device for controlling internal systems within a vehicle based on user preferences. The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope and spirit of disclosed embodiments being indicated by the following claims.

What is claimed is:

1. A method for controlling internal systems within a vehicle, the method comprising:
    detecting, by a floor mat, presence of a user seated on a seat within the vehicle;
    capturing, by the floor mat, at least one user characteristic associated with the user in response to detecting presence of the user;
    controlling, by the floor mat, at least one internal system within the vehicle based on the at least one user characteristic, wherein the floor mat communicates with a central controller in the vehicle to control the at least one internal system;
    creating, by the floor mat, a mapping between user characteristics and user preferences for each of a plurality of registered users; and
    storing, by the floor mat, the mapping inside a storage device within the vehicle for a plurality of registered users, wherein the storage device is communicatively coupled with the central controller.

2. The method of claim 1, wherein the user preferences comprise at least one of cabin temperature, deodorizer settings, sound level of audio system, light intensity, fan speed, seat vibration, backrest heating, seat height, length or inclination.

3. The method of claim 1, wherein controlling comprises matching the at least one user characteristic associated with the user within the mapping.

4. The method of claim 3 further comprises activating the at least one internal system based on user preferences associated with the user, when the user is one of the plurality of registered users and the at least one user characteristic matches with one or more characteristics in the mapping stored in the storage device.

5. The method of claim 3 further comprises activating the at least one internal system based on a default mode, when the user is not a registered user and the at least one user characteristic do not match with one or more characteristics in the mapping stored in the storage device.

6. The method of claim 1, wherein the floor mat comprises at least one of a resistive mesh and a Light Detection and Ranging (LIDAR) module, and wherein the at least one of the resistive mesh and the LIDAR module capture the at least one user characteristic.

7. The method of claim 6, wherein the resistive mesh in the floor mat captures the at least one user characteristic, when one or more feet of the user are in contact with the floor mat and the LIDAR module captures the at least one user characteristic when each feet of the user are not in contact with the floor mat.

8. The method of claim 1, wherein the at least user characteristic comprises at least one of size of a user's foot, weight of a user's foot, shape of a user's foot, or pressure points activated by a user's foot on the floor mat.

9. A floor mat for controlling internal systems within a vehicle, the floor mat comprising:
    at least one senor configured to:
    detect presence of a user seated on a seat within the vehicle; and
    capture at least one user characteristic associated with the user in response to detecting presence of the user; and
    a transceiver communicatively coupled to the at least one sensor, wherein the transceiver is configured to transmit at least one user characteristic to a central controller, wherein the central controller control at least one internal system within the vehicle based on the at least one user characteristic, wherein the at least one sensor comprises at least one of a resistive mesh and a Light Detection and Ranging (LIDAR) module, and wherein the at least one of the resistive mesh and the LIDAR module capture the at least one user characteristic.

10. The floor mat of claim 9, wherein the resistive mesh in the floor mat captures the at least one user characteristic, when one or more feet of the user are in contact with the floor mat and the LIDAR module captures the at least one user characteristic when each feet of the user are not in contact with the floor mat.

11. The floor mat of claim 9, wherein the at least user characteristic comprises at least one of size of a user's foot, weight of a user's foot, shape of a user's foot, or pressure points activated by a user's foot on the floor mat.

12. A system for controlling internal systems within a vehicle, the system comprising:
    a floor mat comprising at least one senor configured to:
        detect presence of a user seated on a seat within the vehicle; and
        capture at least one user characteristic associated with the user in response to detecting presence of the user; and
    a central controller communicatively coupled the floor mat, wherein the central controller is configured to:
        control at least one internal system within the vehicle based on the at least one user characteristic, wherein the central controller is further configured to create a mapping between user characteristics and user preferences for each of a plurality of registered users.

13. The system of claim 12 further comprising a memory configured to store the mapping for a plurality of registered users, wherein the memory is communicatively coupled with the central controller.

14. The system of claim 12, wherein the user preferences comprise at least one of cabin temperature, deodorizer settings, sound level of audio system, light intensity, fan speed, seat vibration, backrest heating, seat height, length or inclination.

15. The system of claim 12, wherein the central controller is further configured to match the at least one user characteristic associated with the user within the mapping.

16. The system of claim 15, wherein the central controller is further configured to activate the at least one internal system based on user preferences associated with the user, when the user is one of the plurality of registered users and the at least one user characteristic matches with one or more characteristics in the mapping stored in the storage device.

17. The system of claim 15, wherein the central controller is further configured to activate the at least one internal system based on a default mode, when the user is not a registered user and the at least one user characteristic do not match with one or more characteristics in the mapping stored in the storage device.

* * * * *